United States Patent [19]

Hisamoto et al.

[11] Patent Number: 4,472,294

[45] Date of Patent: Sep. 18, 1984

[54] FLUORINE-CONTAINING COMPOUNDS, AND SURFACE-TENSION LOWERING AGENT CONTAINING SAME

[75] Inventors: Iwao Hisamoto, Suita; Chiaki Maeda, Kyoto; Mitsuhiro Nishiwaki, Osaka, all of Japan

[73] Assignee: Daikin Kogyo Co., Ltd., Osaka, Japan

[21] Appl. No.: 343,901

[22] Filed: Jan. 29, 1982

[30] Foreign Application Priority Data

Jan. 30, 1981 [JP] Japan .................................. 56-13534

[51] Int. Cl.³ ...................... B01F 17/34; B01F 17/42; B01F 17/44; C07C 67/03
[52] U.S. Cl. ...................................... 252/356; 8/907; 252/3; 252/8.05; 252/351; 252/DIG. 1; 430/493; 526/911; 560/240; 560/264; 568/615; 568/683
[58] Field of Search .................. 252/3, 8.05, 351, 356, 252/DIG. 1; 560/240, 264; 568/615, 683

[56] References Cited

U.S. PATENT DOCUMENTS 1,970,578  8/1934  Schoeller et al. ............. 252/DIG. 1
2,260,753 10/1941  Marple et al. .................. 560/264 X
3,081,354  3/1963  Gaertner et al. ............... 252/351 X
4,165,338  8/1979  Katsushima et al. ........... 560/170 X
4,278,552  7/1981  Hisamoto et al. ...................... 252/3
4,303,534 12/1981  Hisamoto et al. ...................... 252/3

FOREIGN PATENT DOCUMENTS 644828 10/1950  United Kingdom ............... 560/263

Primary Examiner—Richard D. Lovering
Attorney, Agent, or Firm—Birch, Stewart, Kolasch & Birch

[57] ABSTRACT

A fluorine-containing compound of the formula:

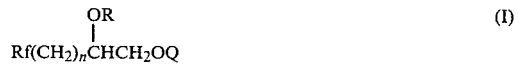

$$Rf(CH_2)_n\underset{|}{\overset{OR}{C}}HCH_2OQ \qquad (I)$$

wherein Rf is a $C_3$–$C_{21}$ fluorine-containing group; R is a hydrogen atom or a $C_1$–$C_4$ acyl group; Q is an aliphatic or aromatic hydrocarbon group having not more than twenty-one carbon atoms; and n is an integer of 1 to 10 lowers the surface tensions of water and/or organic liquids and the interfacial tensions between them.

20 Claims, No Drawings

FLUORINE-CONTAINING COMPOUNDS, AND SURFACE-TENSION LOWERING AGENT CONTAINING SAME

This invention relates to novel fluorine-containing compounds, and their preparation and use. More particularly, it relates to nonionic compounds having a fluorine-containing group and an ether group, a process for preparing the nonionic compounds and a surface-tension lowering agent for water and/or organic liquids comprising the nonionic compounds.

A fluorine-containing compound which effectively lowers the surface tensions of water and of various organic liquids is used, for example, as an additive for a foam fire-extinguisher, a penetrating agent and a leveling agent for resinous compounds. Particularly, a nonionic fluorine-containing compound is widely employed, because it does not afford any unfavorable influence on the other components in a composition into which it is incorporated.

However, conventional nonionic fluorine-containing compounds do not lower the surface tension of liquids, especially of water, as effectively as ionic fluorine-containing surfactants such as anionic or cationic surfactants. Generally, a nonionic fluorine-containing compound which greatly lowers the surface tension of water does not effectively lower the surface tension of organic liquids such as toluene, methylethylketone or dimethylformamide. Thus, a nonionic fluorine-containing compound which can lower the surface tension of organic liquids as well as that of water was not known, and its discovery has been highly desired.

As a result of an extensive study, it has been found that a fluorine-containing compound of the formula:

$$Rf(CH_2)_nCHCH_2OQ \quad \quad (I)$$
$$\overset{|}{OR}$$

wherein Rf is a $C_3-C_{21}$ fluorine-containing group; R is a hydrogen atom or a $C_1-C_4$ acyl group; Q is an aliphatic or aromatic hydrocarbon group having not more than twenty-one carbon atoms; and n is an integer of 1 to 10 effectively lowers the surface tension of water and/or organic liquids.

In the formula (I), Rf is a $C_3-C_{21}$, preferably $C_5-C_{21}$, fluorine-containing group, which may be saturated or unsaturated, straight or branched, or substituted or unsubstituted and may have an oxygen atom(s) in the main chain. R is a hydrogen atom or a $C_1-C_4$ acyl group. The acyl group may be alkanoyl such as formyl, acetyl, propionyl, butyryl and iso-butyryl. Q is an aliphatic or aromatic hydrocarbon group having not more than twenty-one carbon atoms, specific examples of which are alkyl, alkenyl, polyoxyalkylene and phenyl. These groups may be substituted optionally with a suitable substituent such as fluorine, hydroxyl, $C_1-C_5$ alkyl, phenyl, $C_7-C_{10}$ aralkyl, $C_7-C_{21}$ alkylaryl, $C_1-C_{15}$ alkoxy, $C_1-C_5$ alkanoyl, $C_1-C_{10}$ alkylamino and $C_1-C_5$ alkylthio.

Specific examples of the compound (I) are as follows:

$$C_9F_{19}CH_2\overset{|}{\underset{OH}{C}}HCH_2OC_2H_5 \quad (Ia)$$

$$C_8F_{17}(CH_2)_2\overset{|}{\underset{OH}{C}}HCH_2OC_{18}H_{37} \quad (Ib)$$

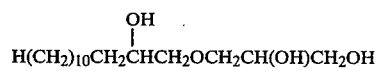  (Ic)

$$C_9F_{19}CH_2\overset{|}{\underset{OH}{C}}HCH_2O(CH_2)_2OH \quad (Id)$$

$$H(CH_2)_{10}CH_2\overset{|}{\underset{OH}{C}}HCH_2OCH_2CH(OH)CH_2OH \quad (Ie)$$

$$C_3F_7O(C_3F_6O)_3\overset{|}{\underset{CF_3}{C}}F-CH_2\overset{|}{\underset{OH}{C}}HCH_2O[(CH_2)_2O]_3H \quad (If)$$

$$C_5F_{11}(CH_2)_6\overset{|}{\underset{OH}{C}}HCH_2O[(CH_2)_2O]_5H \quad (Ig)$$

$$C_9F_{19}CH_2\overset{|}{\underset{OH}{C}}HCH_2O[(CH_2)_2O]_{10}CH_3 \quad (Ih)$$

$$C_{15}F_{31}CH_2\overset{|}{\underset{OH}{C}}HCH_2O[(CH_2)_2O]_{20}H \quad (Ii)$$

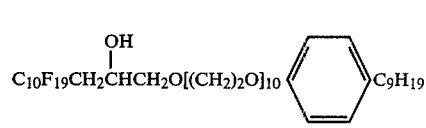  (Ij)

$$C_5F_{11}CH_2\overset{|}{\underset{OH}{C}}HCH_2O(CH_2)_2OCH_2\overset{|}{\underset{OH}{C}}HCHCH_2C_5F_{11} \quad (Ik)$$

$$C_9F_{17}CH_2\overset{|}{\underset{OCOCH_3}{C}}HCH_2O(CH_2)_3N(C_8H_{17})_2 \quad (Il)$$

$$C_{11}F_{23}CH_2\overset{|}{\underset{OH}{C}}HCH_2O(CH_2)_2OCOC_4H_9 \quad (Im)$$

$$H(CF_2)_{12}CH_2\overset{|}{\underset{OCOC_2H_5}{C}}HCH_2OCH_2(CF_2)_2H \quad (In)$$

$$C_5F_{11}CH_2\overset{|}{\underset{OH}{C}}HCH_2O(CH_2)_4SCH_3 \quad (Io)$$

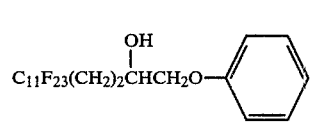  (Ip)

The fluorine-containing compound (I) of the invention may be prepared by reacting a fluorine-containing epoxide of the formula:

$$Rf(CH_2)_n\underset{O}{\overset{\diagdown\diagup}{CH-CH_2}} \quad (II)$$

wherein Rf and n are each as defined above with a compound of the formula:

$$QOH \quad (III)$$

wherein Q is as defined above.

The reaction can be carried out in the presence of a catalyst, if desired, in a solvent at a temperature of from 30° to 150° C., preferably from 50° to 120° C. with stirring. Specific examples of the catalyst are halides of metals belonging to any of the second to fifth and eighth groups of the periodic table (e.g. $ZnCl_2$, $AlCl_3$, $SnCl_4$, $SbCl_5$, $FeCl_3$), $BF_3$(usually in the form of complex with ethers or alcohols), an acid catalyst (e.g. sulfuric acid, sodium hydrogensulfate), etc. Among them, $BF_3$ or its complex is preferred, since it greatly accelerates the reaction rate but affords only a small amount of by-products. The catalyst is used in an amount of 0.01 to 2% by weight based on the weight of the fluorine-containing epoxide (II).

The fluorine-containing compound (I) wherein R is an acyl group may be prepared by reacting the fluorine-containing compound (I) wherein R is a hydrogen atom with an acylating agent such as an acid halide and an acid anhydride.

One of the advantages of the process of the invention using the fluorine-containing epoxide (II) as the starting material is that the reaction can be carried out more efficiently than a conventional process in which an alkylene oxide is added to a fluorine-containing compound.

The capability of the fluorine-containing compound (I) to lower the surface tensions of water and/or various organic liquids and the interfacial tensions between them can be controlled by selection of an appropriate group for Q. Thus, the fluorine-containing compound (I) being remarkable in both of the above performances is readily obtainable by choice of a suitable substituent for Q.

For the use in aqueous solutions, the fluorine-containing compound (I) is preferred to contain any hydrophilic group such as polyoxyethylene for Q. Taking the water solubility into consideration, the degree of polymerization of the polyoxyethylene group may be not less than 3, preferably not less than 5. However, such a high degree of polymerization as more than 40 is not favorable, because the surface tension lowering potency per unit weight is rather decreased while the minimum surface tension is increased. When the fluorine-containing compound (I) bears a lipophilic group such as alkyl or aryl in addition to a hydrophilic group such as polyoxyethylene, its lowering performance onto the interfacial tension between water and an organic liquid is more excellent than that of the corresponding one bearing no lipophilic group.

In the case of using as a surface tension-lowering agent for organic liquids, the fluorine-containing compound (I) is required to have a lipophilic group such as an alkyl group optionally bearing any substituent. In general, the fluorine-containing compound (I) shows a higher solubility into organic liquids with a higher proportion of the lipophilic group in the entire molecule, but the minimum surface tension tends to be increased with the proportion of the lipophilic group. Accordingly, the molecular weight of the Q portion is favorable to be smaller insofar as the fluorine-containing compound (I) is soluble in the organic liquid, usually in a concentration of 0.001% by weight or more.

Since the fluorine-containing compound (I) of the invention is highly effective in lowering the surface tensions of water and/or organic liquids and the interfacial tensions between them, it may be used as an additive for fire-extinguishers (e.g. film foam fire-extinguishers, synthetic surfactant fire-extinguishers, protein foam fire-extinguishers, powder fire-extinguishers), a levelling agent for waxes and paints (e.g. magnetic paints), a penetrating agent for fiber-coloring liquids, metal processing solutions and photographic processing solutions, etc. Further, it may be used as a stripping or releasing agent for resins or as an emulsifier in polymerization. Furthermore, it may be incorporated into resins to impart thereto a fog-resistance, a sliding property, etc.

The amount of the fluorine-containing compound (I) to be used is widely varied with the purpose but may be usually from 0.001 to 5% by weight, preferably from 0.001 to 2% by weight based on the weight of the base material.

The present invention will be illustrated in detail by the following Examples wherein % is by weight.

EXAMPLE 1

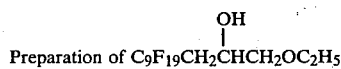

Preparation of $C_9F_{19}CH_2CHCH_2OC_2H_5$ with OH on the CH

Into a 200 ml volume four-necked flask equipped with a thermometer, a condenser and a stirrer,

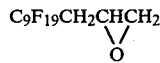

$C_9F_{19}CH_2CHCH_2$ with epoxide O bridge (52.6 g, 0.10 mol), ethanol (46 g, 1.0 mol) and boron trifluoride etherate (0.50 g) were charged and stirred for four hours on a water bath maintained at 60° C. By gas chromatography (FID, column: silicone SE-30 (1 m); column temperature: 100°–250° C.; heating rate: 10° C./min.), it was confirmed that the entire amount of the epoxide was consumed and the desired product was formed. From the reaction mixture, excess ethanol was evaporated off, and thereafter the residue was washed with a mixed solvent of acetonitrile and trichlorotrifluoroethane (50:50 by weight) several times to give a viscous liquid product (48 g). Yield: 84%. B.P.>200° C.

The product was identified as the entitled compound by GC-MS analysis, the conditions and results of which were as follows:

| Apparatus: | Shimadzu LKB-9000. |
|---|---|
| Gas chromatography: | Same as described above (but the carrier gas was helium). |
| Ionization potential: | 70 eV. |
| Main Peak (m/e) | Ionic Species |
| 555 | $[C_9F_{19}CH_2CHCH_2OC_2H_5]^+$ |
| 543 | $[C_9F_{19}CH_2CHCH_2O]^+$ with OH |
| 513 | $[C_9F_{19}CH_2CH]^+$ with OH |
| 59 | $[CH_2OC_2H_5]^+$ |

EXAMPLE 2

Preparation of C$_9$F$_{19}$CH$_2$CH(OH)CH$_2$O(CH$_2$)$_2$OCH$_3$

In the same flask as used in Example 1,

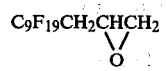

(120 g, 0.23 mol), methylCellosolve (17.3 g, 0.23 mol) and boron trifluoride etherate (1.0 g) were charged and stirred for five hours on a water bath maintained at 70° C. By gas chromatography, it was confirmed that almost the entire amounts of the epoxide and the methylCellosolve were consumed and the desired product was formed. The reaction mixture was washed with a mixed solvent of acetonitrile and trichlorotrifluoroethane (50:50 by weight) several times to give a viscous liquid product (129 g). Yield: 93%. B.P.>200° C.

The product was identified as the entitled compounds by GC-MS analysis under the same conditions as in Example 1, the results of which were as follows:

| Main Peak (m/e) | Ionic Species |
|---|---|
| 603 | [C$_9$F$_{19}$CH$_2$CH(OH)CH$_2$O(CH$_2$)$_2$OCH$_3$ + H]$^+$ |
| 527 | [C$_9$F$_{19}$CH$_2$CH(OH)CH$_2$]$^+$ |
| 89 | [CH$_2$O(CH$_2$)$_2$OCH$_3$]$^+$ |
| 59 | [(CH$_2$)$_2$OCH$_3$]$^+$ |

EXAMPLE 3

Preparation of C$_9$F$_{19}$CH$_2$CH(OH)CH$_2$O— 

Into the same flask as used in Example 1,

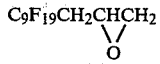

(120 g, 0.23 mol), phenol (21.4 g, 0.23 mol) and sodium hydrogensulfate (1.0 g) were charged and stirred for six hours on a water bath maintained at 70° C. By gas chromatography, it was confirmed that almost the entire amounts of the epoxide and the phenol were consumed and the desired product was formed. The reaction mixture was dissolved in ethanol. Sodium hydrogensulfate was filtered off, and the ethanol was evaporated. Then, the residue was washed with a mixed solvent of acetonitrile and trichlorotrifluoroethane (50:50 by weight) to give a viscous liquid product (132 g). Yield: 93%. B.P.>200° C.

The product was identified as the entitled compound by GC-MS analysis under the same conditions as in Example 1, the results of which were as follows:

| Main Peak (m/e) | Ionic Species |
|---|---|
| 620 | [C$_9$F$_{19}$CH$_2$CH(OH)CH$_2$O—C$_6$H$_5$]$^+$(M) |
| 601 | [M − F]$^+$ |
| 107 | [CH$_2$O—C$_6$H$_5$]$^+$ |

EXAMPLE 4 AND COMPARATIVE EXAMPLE 1

A 0.5% aqueous solution of the fluorine-containing compound (surfactant) as listed in Table 1 was prepared. The surface tension of the solution (Examples 4(1) to 4(4)) or water (Comparative Example 1) and the interfacial tension between the solution and n-hexane (Examples 4(1) to 4(4)) or between water and n-hexane (Comparative Example 1) were measured at 25° C. by the Wilhelmy method (apparatus: Shimadzu ST-1). The results are shown in Table 1.

TABLE 1

| Example | Fluorine-Containing Compound | Surface Tension (dyn/cm) | Interfacial Tension (dyn/cm) |
|---|---|---|---|
| 4(1) | C$_5$F$_{11}$(CH$_2$)$_6$CH(OH)CH$_2$O(CH$_2$CH$_2$O)$_5$H | 23.3 | 9.5 |
| 4(2) | C$_9$F$_{19}$CH$_2$CH(OH)CH$_2$O(CH$_2$CH$_2$O)$_{10}$CH$_3$ | 17.6 | 7.1 |
| 4(3) | C$_{15}$F$_{31}$CH$_2$CH(OH)CH$_2$O(CH$_2$CH$_2$O)$_{20}$H | 19.2 | 8.2 |
| 4(4) | C$_9$F$_{19}$CH$_2$CH(OH)CH$_2$O(CH$_2$CH$_2$O)$_{10}$—C$_6$H$_4$—C$_9$H$_{19}$ | 19.6 | 4.8 |
| Comparative Example 1 | — | 72.0 | 51.3 |

EXAMPLE 5 AND COMPARATIVE EXAMPLES 2 TO 4

A 0.5% solution of the fluorine-containing compound (surfactant) as listed in Table 2 in an organic solvent (i.e. dimethylformamide, methylethylketone, toluene) was prepared. The surface tension of the organic solution (Examples 5 (1) to 5(5) and Comparative Examples 3 and 4) or the organic solvent (Comparative Example 2) was measured at 25° C. by the Wilhelmy method. The fluorine-containing compound used in Comparative Example 3 was a cationic surfactant, and that used in Example 4 was an anionic surfactant. The results are shown in Table 2.

TABLE 2

| | Fluorine-Containing Compound | Organic Solvent DMF*1 | MEK*2 | Toluene |
|---|---|---|---|---|
| Example 5(1) | $C_9F_{19}CH_2\overset{OH}{\underset{\|}{C}}HCH_2OC_2H_5$ | 18.9 | 19.6 | 21.5 |
| Example 5(2) | $C_9F_{19}CH_2\overset{OH}{\underset{\|}{C}}HCH_2O$ 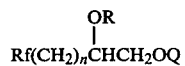 | 18.5 | 20.3 | 21.4 |
| Example 5(3) | $C_{11}F_{23}CH_2\overset{OH}{\underset{\|}{C}}HCH_2O(CH_2)_2OCOC_4H_9$ | 20.6 | 21.4 | 22.8 |
| Example 5(4) | $C_9F_{19}CH_2\overset{OH}{\underset{\|}{C}}HCH_2O(CH_2)_2OCH_3$ | 19.2 | 20.5 | 22.4 |
| Example 5(5) | $C_5F_{11}CH_2\overset{OCOC_2H_5}{\underset{\|}{C}}HCH_2OC_4H_4SCH_3$ | 22.4 | 23.2 | 23.6 |
| Comparative Example 2 | — | 35.4 | 24.1 | 28.0 |
| Comparative Example 3 | $C_9F_{19}CH_2CH(OH)CH_2\overset{+}{\underset{\underset{CH_3}{\|}}{N}}(C_2H_5)_2.I^-$ | 34.9 | 24.0 | 27.8 |
| Comparative | $C_9F_{19}COO^-.H_3\overset{+}{N}(CH_2)_3OH$ | 34.0 | 24.1 | 4 |

Note
*1Dimethylformamide
*2Methylethylketone

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A fluorine-containing compound of the formula:

$$Rf(CH_2)_n\overset{OR}{\underset{\|}{C}}HCH_2OQ \quad (I)$$

wherein Rf is a $C_3$–$C_{21}$ fluorine-containing group; R is a hydrogen atom or a $C_1$–$C_4$ acyl group; Q is an alkyl, alkenyl, polyoxyalkylene or aromatic hydrocarbon group which is optionally substituted with at least one substituent selected from the group consisting of fluorine, hydroxyl, $C_1$–$C_5$ alkyl, phenyl, $C_7$–$C_{10}$ aralkyl, $C_7$–$C_{21}$ alkylaryl, $C_1$–$C_{15}$ alkoxy, $C_1$–$C_5$ alkanoyl, $C_1$–$C_{10}$ alkylamino and $C_1$–$C_5$ alkylthio and the total number of the carbon atoms of which is not more than 42; and n is an integer of 1 to 10.

2. The compound according to claim 1 wherein Rf is a $C_5$–$C_{21}$ fluorine-containing group.

3. The compound according to claim 1 wherein R is a hydrogen atom.

4. The compound according to claim 1 wherein R is a $C_1$–$C_4$ acyl group.

5. The compound according to claim 1 wherein Q is an alkyl group or an alkenyl group.

6. The compound according to claim 1 wherein Q is a polyoxyalkylene group.

7. The compound according to claim 6 wherein the degree of polymerization of the polyoxyalkylene group is at least 3.

8. The compound according to claim 6, wherein the degree of polymerization of the polyoxyalkylene group is at least 5.

9. A fluorine-containing compound according to claim 1 of the formula:

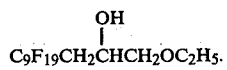

$C_9F_{19}CH_2\overset{OH}{\underset{\|}{C}}HCH_2OC_2H_5.$

10. A fluorine-containing compound according to claim 1 of the formula:

$C_9F_{19}CH_2\overset{OH}{\underset{\|}{C}}HCH_2O(CH_2)_2OCH_3.$

11. A fluorine-containing compound according to claim 1 of the formula:

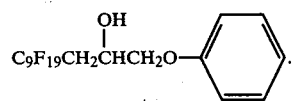

12. A fluorine-containing compound according to claim 1 of the formula:

$$C_5F_{11}(CH_2)_6\overset{\underset{\displaystyle |}{OH}}{C}HCH_2O(CH_2CH_2O)_5H.$$

13. A fluorine-containing compound according to claim 1 of the formula:

$$C_9F_{19}CH_2\overset{\underset{\displaystyle |}{OH}}{C}HCH_2O(CH_2CH_2O)_{10}CH_3.$$

14. A fluorine-containing compound according to claim 1 of the formula:

$$C_{15}F_{31}CH_2\overset{\underset{\displaystyle |}{OH}}{C}HCH_2O(CH_2CH_2O)_{20}H.$$

15. A fluorine-containing compound according to claim 1 of the formula:

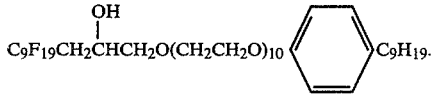

16. A fluorine-containing compound according to claim 1 of the formula:

$$C_{11}F_{23}CH_2\overset{\underset{\displaystyle |}{OH}}{C}HCH_2O(CH_2)_2OCOC_4H_9.$$

17. A fluorine-containing compound according to claim 1 of the formula:

$$C_3F_7O(C_3F_6O)_3\overset{\underset{\displaystyle |}{CF_3}}{C}F-CH_2\overset{\underset{\displaystyle |}{OH}}{C}HCH_2O[(CH_2)_2O]_3H.$$

18. A fluorine-containing compound according to claim 1 of the formula:

$$C_9F_{19}CH_2\overset{\underset{\displaystyle |}{OH}}{C}HCH_2O(CH_2)_2OH.$$

19. A fluorine-containing compound according to claim 1 of the formula:

$$C_5F_{11}CH_2\overset{\underset{\displaystyle |}{OCOC_2H_5}}{C}HCH_2OC_4H_4SCH_3.$$

20. A surface-tension lowering agent for water and/or organic liquids consisting essentially of a compound of the formula:

$$Rf(CH_2)_n\overset{\underset{\displaystyle |}{OR}}{C}HCH_2OQ \quad (I)$$

wherein Rf is a $C_3$–$C_{21}$ fluorine-containing group; R is a hydrogen atom or a $C_1$–$C_4$ acyl group; Q is an alkyl, alkenyl, polyoxyalkylene or aromatic hydrocarbon group which is optionally substituted with at least one substituent selected from the group consisting of fluorine, hydroxyl, $C_1$–$C_5$ alkyl, phenyl, $C_7$–$C_{10}$ aralkyl, $C_7$–$C_{21}$ alkylaryl, $C_1$–$C_{15}$ alkoxy, $C_1$–$C_5$ alkanoyl, $C_1$–$C_{10}$ alkylamino and $C_1$–$C_5$ alkylthio and the total number of the carbon atoms of which is not more than 42; and n is an integer of 1 to 10.

* * * * *